(12) United States Patent
Lieberman et al.

(10) Patent No.: US 6,630,947 B1
(45) Date of Patent: Oct. 7, 2003

(54) METHOD FOR EXAMINING SUBSURFACE ENVIRONMENTS

(75) Inventors: Stephen H. Lieberman, La Mesa, CA (US); Pamela A. Boss, San Diego, CA (US); Gregory W. Anderson, San Diego, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/162,418

(22) Filed: Sep. 28, 1998

Related U.S. Application Data (63) Continuation-in-part of application No. 08/630,653, filed on Apr. 10, 1996, now abandoned, which is a continuation-in-part of application No. 08/772,611, filed on Dec. 23, 1996.

(51) Int. Cl.⁷ ................................................ H04N 7/18
(52) U.S. Cl. ........................................................ 348/85
(58) Field of Search ................... 348/85, 132; 358/100; 122/329; 134/1; 359/834, 386; 73/151; 175/4.6, 49; 166/242.1; 356/32, 318, 236, 382, 4; 118/315; 250/341, 458.1; 354/403; 128/664, 665; H04N 7/18

(56) References Cited

U.S. PATENT DOCUMENTS

| | | | | |
|---|---|---|---|---|
| 3,880,176 A | * | 4/1975 | Borne | 134/167 |
| 4,456,401 A | * | 6/1984 | Williams | 405/150 |
| 4,527,893 A | * | 7/1985 | Taylor | 356/4 |
| 4,752,799 A | * | 6/1988 | Stauffer | 354/403 |
| 4,785,336 A | * | 11/1988 | McComb et al. | 356/382 |
| 4,805,450 A | * | 2/1989 | Bennett et al. | 73/155 |
| 4,855,820 A | * | 8/1989 | Barbour | 358/100 |
| 4,899,277 A | * | 2/1990 | Iizuka et al. | 364/422 |
| 4,995,396 A | * | 2/1991 | Inaba et al. | 128/654 |
| 5,014,708 A | * | 5/1991 | Hayashi et al. | 128/653 |
| 5,075,552 A | * | 12/1991 | McClelland et al. | 250/341 |
| 5,088,492 A | * | 2/1992 | Takayama et al. | 128/654 |
| 5,194,193 A | * | 3/1993 | Humphreys et al. | 264/35 |
| 5,251,004 A | * | 10/1993 | Doiron et al. | 356/236 |
| 5,271,380 A | * | 12/1993 | Riek et al. | 128/4 |
| 5,273,871 A | * | 12/1993 | Takda et al. | 430/567 |
| 5,305,759 A | * | 4/1994 | Kaneko et al. | 128/665 |
| 5,376,097 A | * | 12/1994 | Phillips | 606/151 |
| 5,479,024 A | * | 12/1995 | Hillner et al. | 250/458.1 |
| 5,504,788 A | * | 4/1996 | Brooks et al. | 376/248 |
| 5,569,292 A | * | 10/1996 | Scwemberger et al. | 606/185 |
| 5,586,580 A | * | 12/1996 | Fisk et al. | 138/98 |
| 5,633,711 A | * | 5/1997 | Nelson et al. | 356/318 |
| 5,707,389 A | * | 1/1998 | Louw et al. | 606/200 |
| 5,713,364 A | * | 2/1998 | Bebaryshe et al. | 128/664 |

(List continued on next page.)

OTHER PUBLICATIONS

Lieberman et al., "Cone Penetrometer Deployed In Situ Video Imaging System for Characterizing Sub–Surface Soil Properties and Contaminants", *Field Screening Europe*, Oct. 1, 1997, Karlsruhe, Germany, First International Conference on Strategies and Techniques for the Investigation and Monitoring of Contaminated Sites, pp. 129–132.

*Primary Examiner*—Chris Kelley
*Assistant Examiner*—Tung Vo
(74) *Attorney, Agent, or Firm*—Andrew J. Cameron; Michael A. Kagan; Peter A. Lipovsky (57) ABSTRACT

A method for detecting chemical contamination in subsurface environments. The method is implemented using a video imaging system incorporated into a probe than be pushed into soil to collect in situ images. The method is particularly useful for identifying non-aqueous phase liquids (NAPLs) contaminants. Immiscible globules of NAPLs can be detected in the in situ images based on differences in shape and/or color with respect to the soil background. Alternatively, indicator dyes that partition the NAPLs can be released from the sensor probe so that the NAPLs are rendered more easy to detect due to changes in color or a specific fluorescence emission.

11 Claims, 6 Drawing Sheets

U.S. PATENT DOCUMENTS 5,735,955 A * 4/1998 Monaghan et al. ......... 118/317
5,750,355 A * 5/1998 Targan et al. .............. 435/7.24
5,759,773 A * 6/1998 Tyagi et al. ................... 435/6
5,813,985 A * 9/1998 Carroll ....................... 600/436
5,993,378 A * 11/1999 Lemelson ................... 600/109
6,115,061 A * 9/2000 Liebermand et al. ......... 348/85

* cited by examiner

METHOD FOR EXAMINING SUBSURFACE ENVIRONMENTS

This application is a continuation-in-part of application Ser. No. 08/630,653 filed Apr. 10, 1996, now abandoned, and is a continuation-in-part of application Ser. No. 08/772,611, filed Dec. 23, 1996.

FIELD OF THE INVENTION

The present invention relates to a system for examining subsurface environments, and more particularly, to a method for detecting visual images of subsurface geological environments using a soil penetrating probe.

BACKGROUND OF THE INVENTION

Increasing concern with soil and groundwater contamination and governmental mandated requirements to clean up hazardous waste sites have created a need for cost effective systems and methods for determining the characterization of subsurface environments. In response to such needs, soil penetrating probes have been developed. Soil penetrating probes generally comprise a tube having a tapered tip which is forced down into the ground. Instrumentation in the tube detects various properties of the surrounding geological environment.

U.S. Pat. No. 5,128,882, "Device for Measuring Reflectance and Fluorescence of In-situ Soil," describes a soil penetrating probe having an optical fiber, a light source within the interior of the probe, and a transparent window which provides a light port into and out of the probe. Light passes through the transparent window to irradiate the surrounding soil immediately outside of the window as the probe passes through the soil. The irradiated soil reflects light back through the window whereupon the reflected light is collected by a fiber optic link connected to instrumentation on the surface. The collected light then is subjected to spectroanalysis for determining the chemical composition of the soil, particularly with regard to soil contamination. This system only detects the spectral characteristics of the surrounding environment; it cannot provide optical images. Therefore, information such as the porosity and grain size of surrounding soils are not discernible from the type of information provided through spectral analysis. However, porosity and grain size are important characteristics because they are important variables that control the transport of contaminants in soil.

Another soil penetrating probe system is described in U.S. Pat. No. 5,123,492, "Method and Apparatus for Inspecting Subsurface Environments." This system includes a soil penetrating probe having a clear tube in which is suspended a video camera linked to the surface. A significant limitation of this system is that because the camera freely swings within the transparent tube, the focus of the camera with respect to the surrounding geological features is constantly changing and cannot be controlled. Furthermore, the system does not provide any means for illuminating the surrounding subsurface environment other than from ambient light which may happen to filter from the surface down through the tube.

Delineation of Non-Aqueous Phase Liquids (NAPLs) contaminants in the subsurface soil environment is a serious environmental challenge. In particular, locating Dense Non-Aqueous Phase Liquids (DNAPLs) is recognized as one of the most difficult technical challenges currently limiting the clean up of hazardous wastes sites. Much of the problem is because DNAPLs behave differently than most other contaminants. Because they are immiscible with, and denser than, water, they do not accumulate on the surface of ground water, as is usually the case with petroleum hydrocarbon contaminants. Instead, when they are released into the environment as a result of surface spills, tank leaks, and improper disposal practices, they tend to sink through the vadose zone, through the capillary fringe and on into the ground water. As they sink, they can leave behind a trail of micro-globules in the pore spaces of the soil matrix. Because they have relatively high volatilities, residual phase chlorinated solvents in the vadose zone can be transferred quickly into the vapor phase and out of the soil. Consequently, vadose zone contamination is generally not the most significant long-term problem. In contrast, when chlorinated DNAPLs make it into the groundwater, transfer into the vapor phase no longer remains an effective removal mechanism. Instead, the residual immiscible "free-product" phase can slowly dissolve into the groundwater any where from decades to centuries. Even though the solubilities are low enough to allow the residual phase to persist for very long times, the solubilities are high enough to result in water concentrations many orders of magnitude greater than current drinking water quality standards.

The fact that the source of the DNAPL contamination to the groundwater often exists as tiny "micro-globs" of residual free product trapped between individual soil particles is one of the main reasons that site remediation has been so difficult. To make matters even worse, the distribution of these micro-globules is very heterogeneous. It is presently believed that as DNAPLs sink through permeable soils, small quantities of free product are left behind in widely dispersed micro-globules. When the sinking DNAPL encounters a confining layer the DNAPL may accumulate and then spread laterally until it finds a fracture or some other path to the deeper zones. The heterogeneous distribution of NAPLs in the real world that has made delineating these source zones very difficult because most analytical detection schemes depend on point measurements. It is easy to see that if measurements are made at widely spaced intervals (e.g., several feet to tens of feet apart) the likelihood of locating micro globules is very remote.

At present most methods that have been used to attempt to delineate DNAPL distributions do not even attempt to target the free phase product but rather rely on extrapolation of soil gas survey results and coincidental soil and water sampling to predict the location of the source material. Current approaches that depend on use of soil gas methods for identifying free phase DNAPL below the water table are often unreliable because: 1) volatilization of DNAPLs below the water table is not always detectable within the vadose zone, 2) vapor migration pathways do not necessarily match distributions of free phase product, and 3) positive soil gas results do not provide information about the depths of the subaqueous free phase DNAPLs.

There are additional difficulties associated with the use of conventional soil and water sampling methods that depend on drilling, sampling, and laboratory analysis to locate free phase DNAPLs below the water table. Depending upon soil type, the use of conventional split spoon sampling below the water table may be questionable. Unconsolidated sands and silty soils tend to flow in the saturated zone, resulting in poor retention of the sample in the split spoon. Delineation of these subsurface contaminants usually requires trial-and-error placement of a significant number of monitoring wells and extensive sample collection efforts. Laboratory analysis of samples taken in the field is time consuming and costly. Since DNAPLs are volatile, sample-handling problems often lead to questionable analytical results. In addition, conventional sampling procedures that rely on drilling into or through DNAPL zones create an additional problem because they may actually provide new pathways for mobilization of the contaminant. Conventional monitoring techniques that use soil samples taken at selected depth levels along with permanent monitoring wells installed in clusters of two to four at different depths are believed to rarely provide the level of detail needed to provide a reliable picture of the nature and extent of solvent DNAPL below the water table. This belief is based on the understanding that because the distribution of DNAPL solvent distributions is complex, there has rarely been a direct detection of residual or free-phase DNAPL in the groundwater zone even at intensely investigated DNAPL sites.

Thus, there is a continuing need for a method for obtaining visual images of subsurface environments to detect underground chemical contamination, such as NAPLs.

SUMMARY OF THE INVENTION

The invention provides a method for detecting chemical contamination in subsurface environments. The method is implemented using a video imaging system incorporated into a probe than be pushed into soil to collect in situ images. The method is particularly useful for identifying non-aqueous phase liquids (NAPLs) contaminants. Immiscible globules of NAPLs can be detected in the in situ images based on differences in shape and/or color with respect to the soil background. Alternatively, indicator dyes that partition the NAPLs can be released from the sensor probe so that the NAPLs are rendered more easy to detect due to changes in color or a specific fluorescence emission resulting from a chemical interaction between the NAPLs and the indicator dye.

An important advantage of the invention is that it provides a method for directly observing contamination source zones in subsurface soil environments under actual conditions, as opposed to taking core samples.

These and other advantages of the invention will become more apparent upon review of the accompanying text taken in conjunction with the drawings.

BRIEF DESCRIPTION OF THE DRAWINGS

Throughout the several figures like elements are referenced using like reference numbers.

DESCRIPTION OF THE PREFERRED EMBODIMENTS

The present invention provides a method for obtaining visual images of subsurface soil environments to facilitate detection of subsurface chemical contaminants such as NAPLs. The invention employs an optical imaging system incorporated in sensor probe 200 (FIG. 1) hat can be pushed into the soil to collect in situ images of immiscible globules of non-aqueous phase liquids that are trapped in the soil matrix. The in situ video imaging system is described in co-pending and commonly assigned U.S. Pat. application Ser. No. 8/772,611, filed Dec. 23, 1996, incorporated herein by reference. In the simplest case, the immiscible globules of non-aqueous phase liquids present within the viewing range of imaging system may be detected based on differences in shape and/or color with respect to the soil background. Alternatively, indicator dyes (either colormetric or fluorometric) that partition into the non-aqueous phase liquid can be released from the sensor probe so that the non-aqueous phase liquids are rendered more easy to detect due to changes in color or a specific fluorescence emission.

NAPL contaminants include both Light Non-Aqueous Phase Liquids (LNAPLs) and Dense Non-Aqueous Phase Liquids (DNAPLS). LNAPLs include most fuel hydrocarbons such as jet fuel, diesel fuel, lubricating oils, hydraulic fluids, etc.). DNAPLS include most chlorinated solvents such as TCE (Trichloroethylene), PCE (Tetrachloroetylene), and DCE (Dichloroethylene), etc.; halogenated benzenes, polychlorinated biphenyls (PCBs), some pesticides, coal tar and creosote.

Although NAPL contamination may be visualized without any pre-treatment, the visual detection scheme can be enhanced if indicator dyes are used to make the contaminant more visible by dispensing an indicator dye from a port on the probe so that the indicator dye is released below the viewing window of the imaging system. Dispensing an appropriate indicator dye into the soil formation forms a colored (or fluorescent) product with the NAPL (if present) in advance of the imaging system as the probe is pushed into the ground. A system for dispensing the indicator reagent from the probe is also described in application Ser. No. 08/772,611.

Figure 1A:
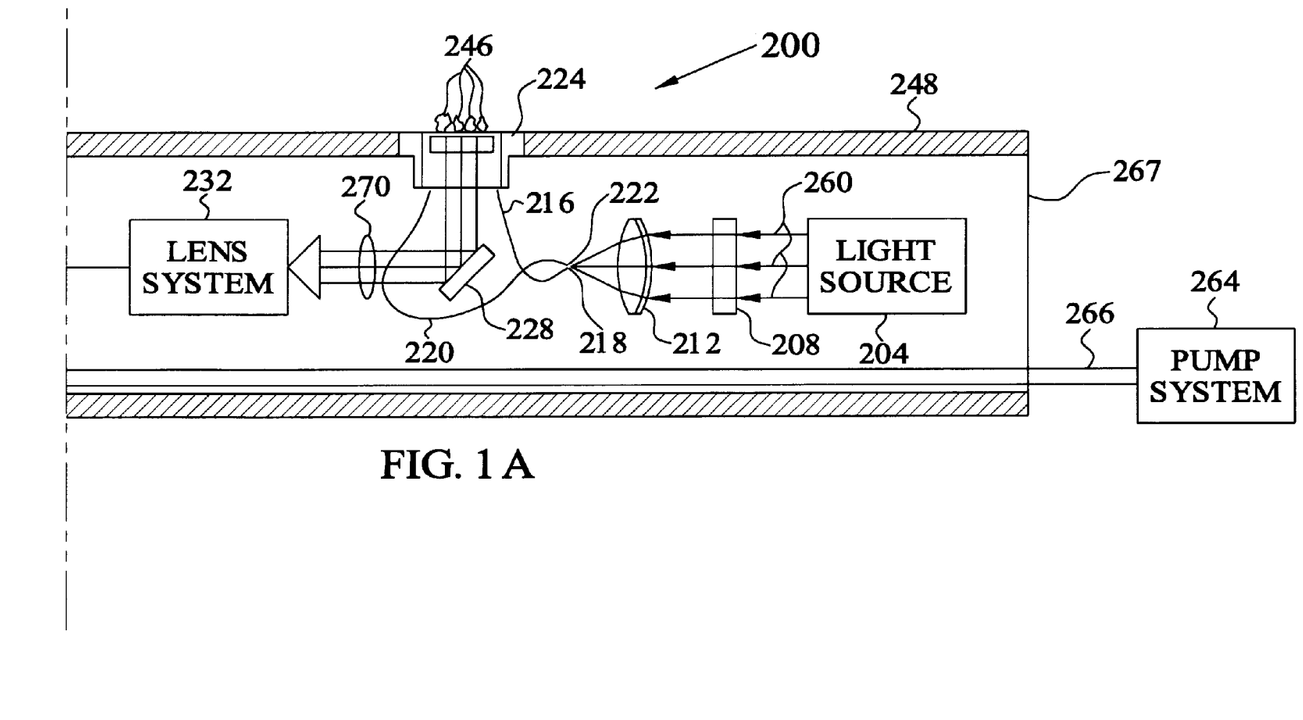
FIG. 1 is a schematic illustration of an in-situ microscope embodying various features of the present invention.
Figure 1B:
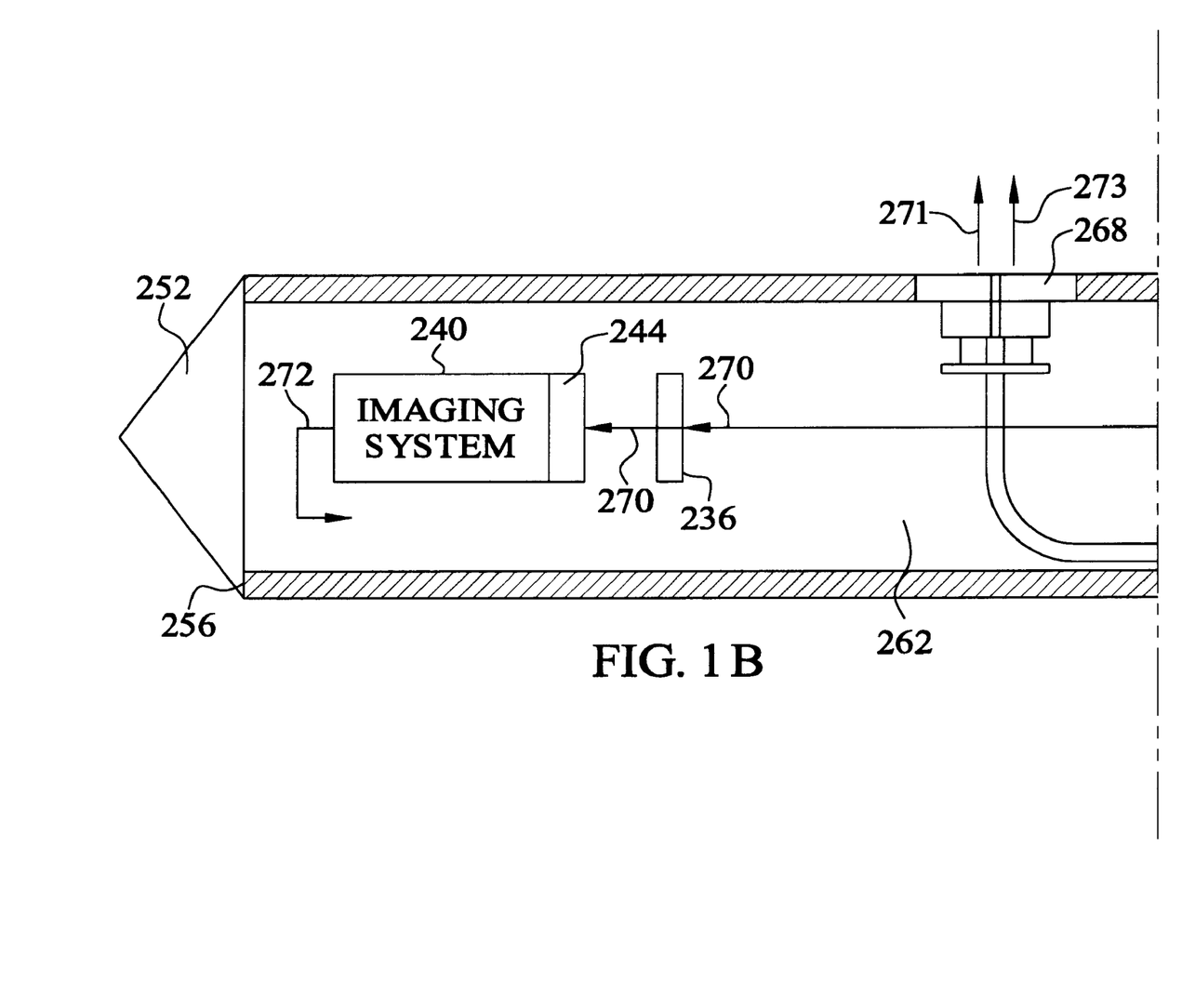
Figure 2:
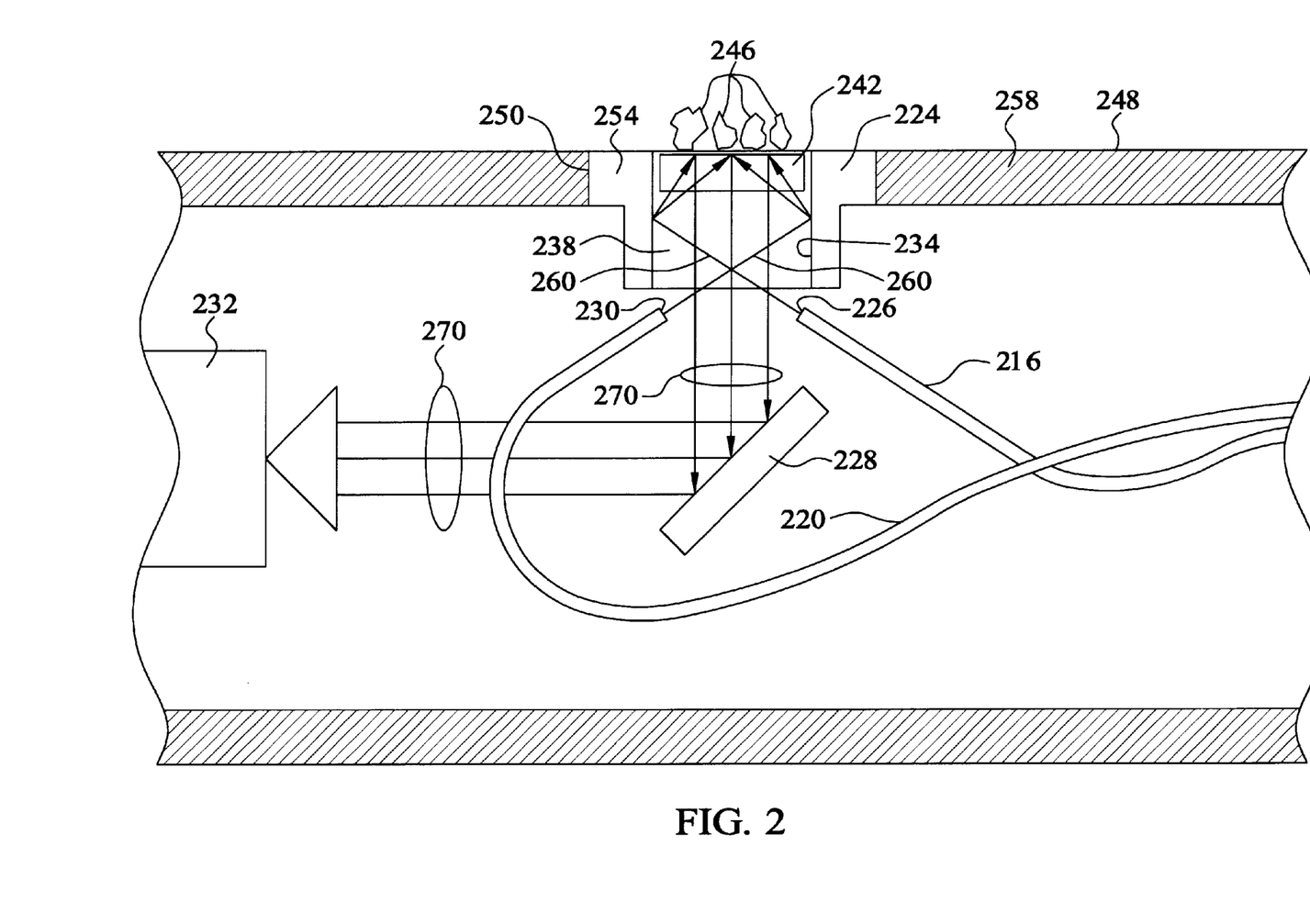
FIG. 2 is an enlarged view of the window housing of the microscope represented in FIG. 1.

In FIGS. 1 and 2 there is shown in situ microscope imaging system 200 which includes a light source 204, an optional optical filter 208, a focusing lens 212, optical fibers 216 and 220, window housing 224, optical reflecting element 228, lens system 232, optional optical filter 236, and imaging system 240, such as a still camera or video camera, having an image detecting area 244, all mounted in a tube 248 having a throughbore 262. A conically shaped tip 252 is mounted to the penetration end 256 of the tube 248. The optical reflecting element 228 may be implemented as a prism or mirror. The window housing 224 includes an insert fitting 254 and a transparent window 242. The insert fitting is fitted through an aperture 250 of sidewall 258 of tube 248. The surface 234 of bore 238 preferably has a surface finish which when illuminated, causes light to be diffused in different directions through the window 242. The light source 204 may be implemented, for example, as a laser, flash lamp, arc-lamp, laser diodes, light emitting diodes, or any other source of optical energy that generates light at wavelengths suitable for a particular application. When implemented as a laser, the light source 204 may be a nitrogen, xenon-chloride, Nd-YAG, or other suitable laser. Lens system 232 may have a fixed focal length or may have a motor driven "zoom" type lens to provide the lens system with an adjustable focal length. In FIG. 1, the light source 204 is shown positioned in the tube 248. However, there may be applications where it is desirable for the light source 204 to be located externally from the tube 248.

Still referring to FIG. 1, light source 204 generates light signals 260 which are directed to focusing lens 212. In some applications, optical filter 208 optionally may be interposed between the lens 212 and light source 204 to filter out undesirable spectral components or to select specific components having particular wavelengths of the light signals 260. Lens 212 focuses light signals 260 onto the bare polished, and preferably bundled ends 218 and 222 of optical fibers 216 and 220, respectively. Light signals 260 propagate through optical fibers 216 and 220. Then, as shown in FIG. 2, the light signals 260 are emitted from the ends 226 and 230 of optical fibers 216 and 220, respectively. Fibers 216 and 220 may be implemented as Ensign-Bickford HCG fiber having a 365 micro meter diameter, although it is to be understood that other fibers having other diameters may also be used. The light signals 260 illuminate the sidewall 324 of bore 238 and are directed at diffuse angles through transparent window 242 to illuminate soil particles 246 outside the window 242. In the preferred embodiment, transparent window 242 may be made of sapphire because it is optically transparent over a broad spectral range and is very hard. The hardness of the window 224 is important in order for the window to withstand the rigors of abrasion as the tube 248 penetrates the soil.

Still referring to FIG. 2, light signals 260 illuminate the soil particles 246. Light signals 270 reflecting from or generated by the illuminated soil particles 246 are directed by optical reflecting element 228 and directed to lens system 232. As shown in FIG. 1, lens system 232 focuses the light signals 270 onto image gathering area 244 of imaging system 240. Optionally, optical filter 236 may be interposed between the focusing system 232 and the imaging system 240 to selectively filter undesirable spectral components or to select specific components, having particular wavelengths, of the light signals 270. The imaging system 240 transforms signals 270 into an output signal 272 which represents an image of the soil particles 246. The output signal 272 may be provided to signal processing equipment, not shown, at the earth's surface.

Figure 4:
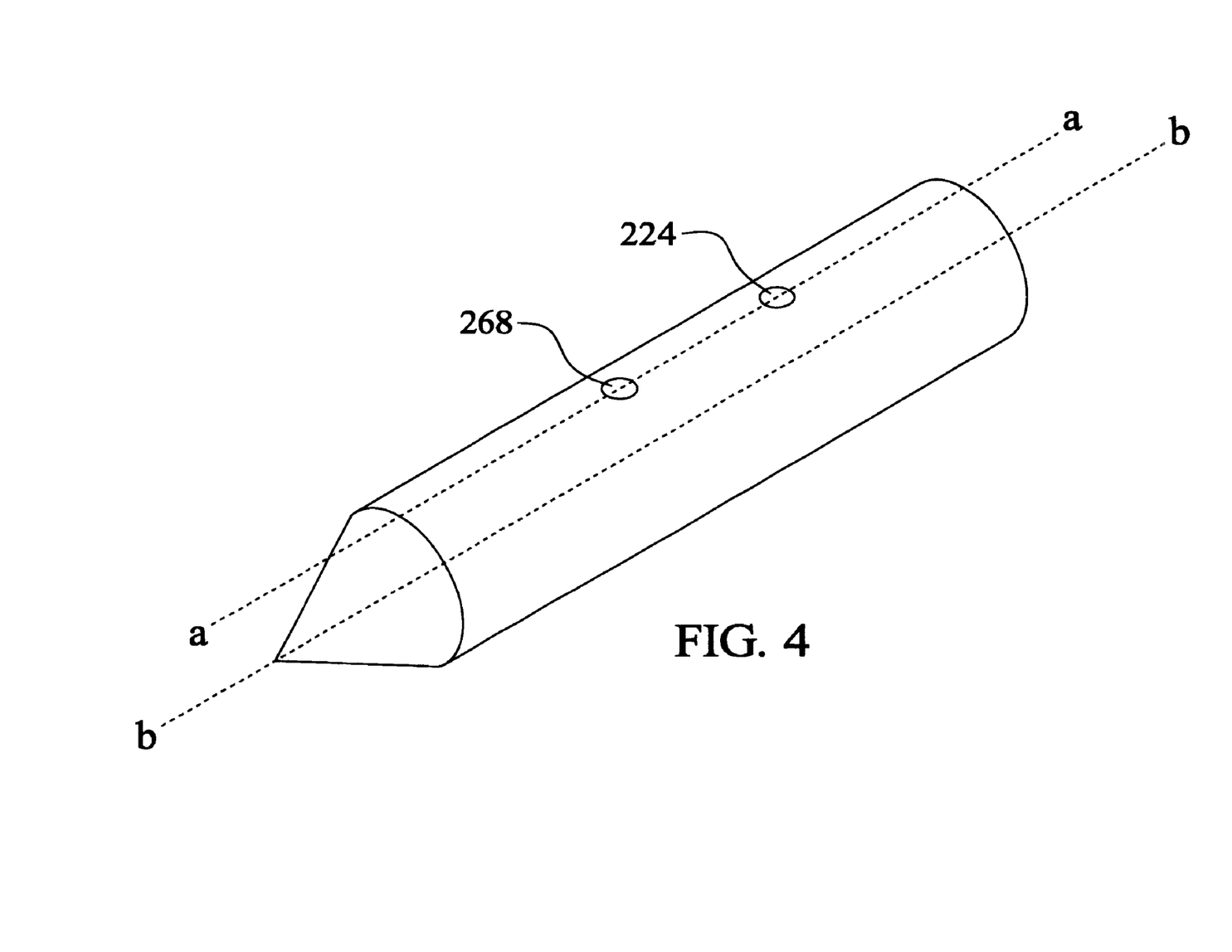
FIG. 4 is a schematic diagram of the indicator reagent delivery system of FIG. 1.

In FIG. 1 microscope imaging system 200 further includes an indicator reagent delivery system comprising a pump system 264 for pumping a reactive fluid 271 through a preferably flexible tube 266 connected through the end 267 of the tube 248 to a nozzle 268. The tube 268 preferably may be implemented as ⅛ inch diameter polypropylene tubing having an inside cross-sectional area of about 0.005 in². Such tubing has a working pressure of 350 psig and a burst pressure of 1400 psig. The nozzle 268 is mounted through the sidewall 258 of tube 248 so that the indicator reagent 271 may be dispensed or pumped from the nozzle 268 into the surrounding soil strata. The indicator reagent 271 is selected to chemically react with certain types of chemicals or micro-biological organisms of interest that may be present in the soil so that they may more easily be detected when illuminated due to a fluorescence or colormetric response of the complex. The nozzle 268 is preferably mounted through the sidewall 258 of tube 248 between the conically shaped tip 252 and window 224 so that, as shown in FIG. 4, the window 224 and nozzle 268 are generally located on a line a—a located on the surface of the tube 248 which is parallel to the longitudinal axis b—b of the tube 248. Therefore, indicator reagent is present in the soil by the time the reagent impregnated soil is viewed through the window 224 as the tube 248 is driven through the soil.

Figure 3:
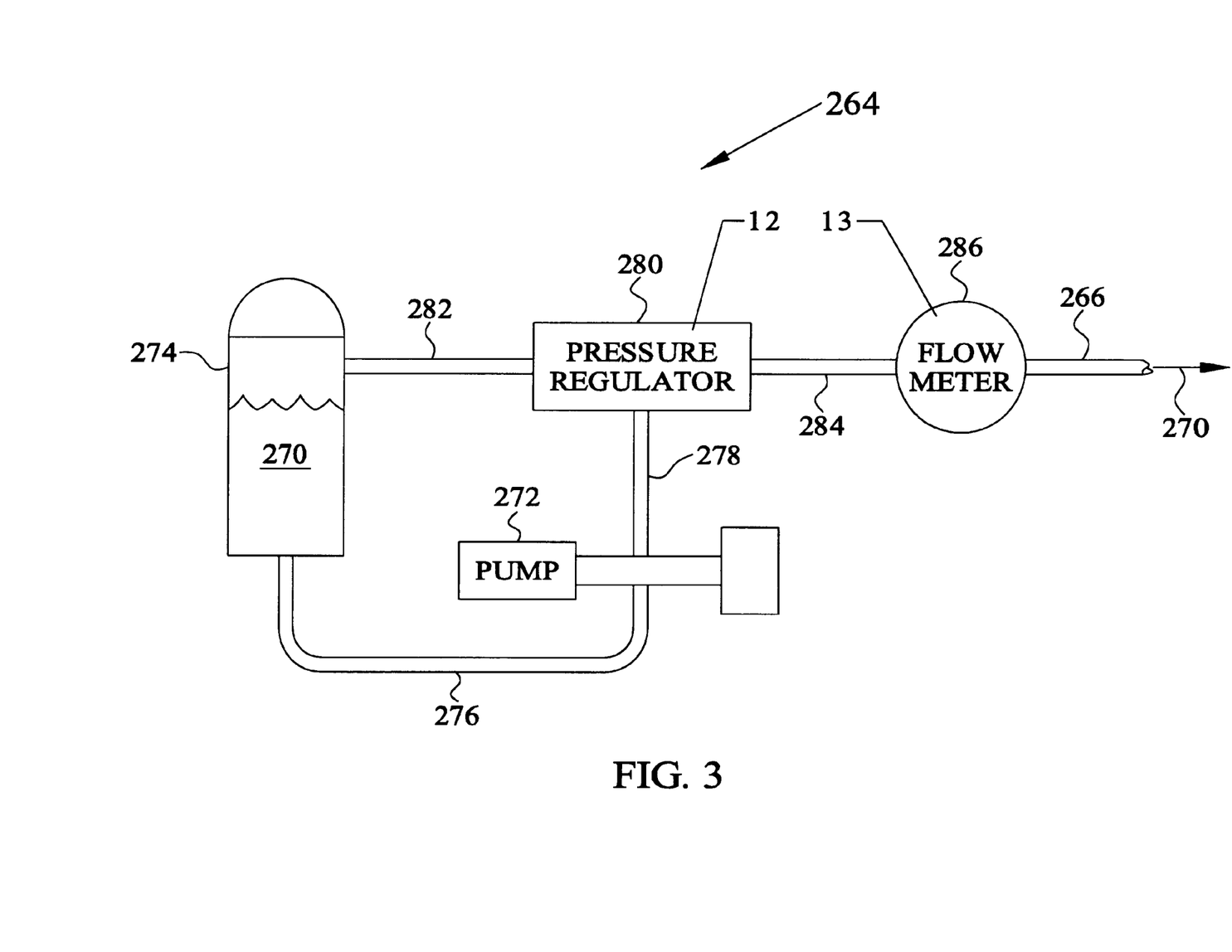
FIG. 3 is a three-quarter exterior view of the system shown in FIG. 5.

Pump circuit 264, shown in FIG. 3, includes a pump 272 which draws indicator reagent 271 from reservoir 274 through supply line 276 and outputs pressurized indicator reagent 271 through pump output line 278 to pressure regulator 280. The pressure regulator 280 regulates the pressure of indicator reagent agent 271 by, inter alia, returning some indicator reagent 271 back to reservoir 274 through bypass flow return line 282. The pressure regulator outputs indicator reagent 271 having a predetermined pressure, via line 284, to flow meter 286 which controls the volume flow of the pressurized indicator reagent 271. The flow regulated output of indicator reagent 271 is delivered to nozzle 228 via conduit 266. The pump may be a Neptune Model 535-S-N3 positive displacement piston/diaphragm pump having stainless steel internal elements, a Teflon™ diaphragm, and inert Viton™ seals so that the pump is chemically resistant to the indicator reagent 271. Like the pump 272, the pressure regulator 280 and flow meter 286 should be corrosion and chemically resistant to the indicator reagent 271. An example of a flow meter suitable for many applications of the invention is a polypropylene bellows type flow meter of the type manufactured by Gorman-Rupp which can accurately regulate the flow of indicator reagent 271 through nozzle 268 from 1.9 ml/min to 5200 ml/min.

Figure 5:
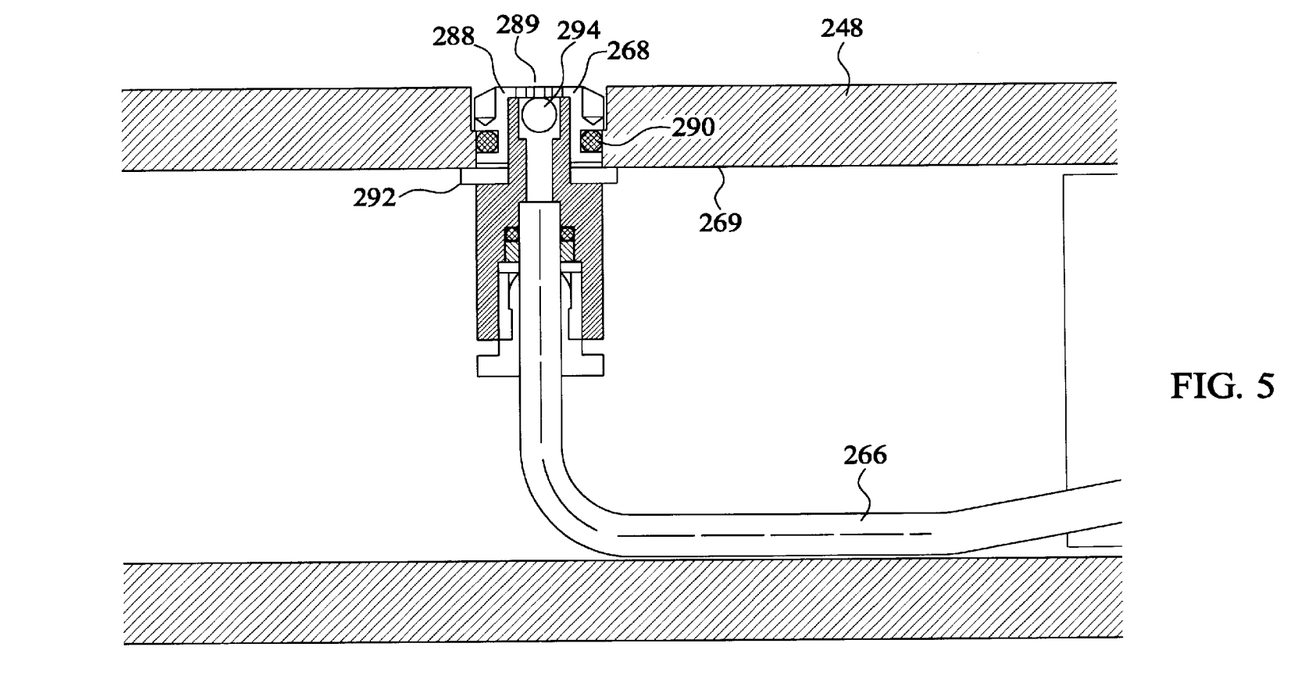
FIG. 5 shows the nozzle assembly of the fluid delivery system used in conjunction with the system shown in FIG. 1.
Figure 6:
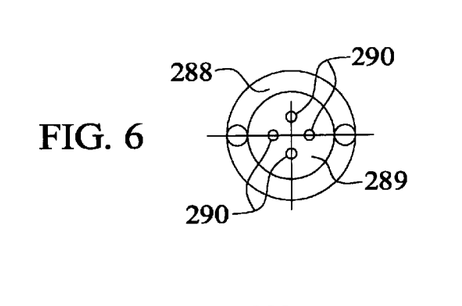
FIG. 6 is a plan view of the nozzle depicted in FIG. 5.

By way of example, as shown in FIG. 5, the nozzle 268 may be implemented as a Prestolok Fitting No. 68PL-2-1-X32 which is positioned through the tube wall 258 using a threaded check housing 288 which includes an O-ring seal 290 that prevents leakage into the tube 248. A contoured washer 292 is positioned between the nozzle 268 and the interior surface 269 of the tube 248 to maintain a tight surface interface between the interior surface 269 and nozzle 268. The nozzle is partially bored out to receive a stainless steel check-ball 294 between the nozzle and the check housing 288. The check-ball 294 prevents external hydrodynamic pressure from forcing fluids from the soil from entering the tube 248. However, the check-ball 294 allows indicator reagent 271 to be pumped out of the nozzle 268. The face 289 of the check housing may include one or more bores 290 through which agent 271 may be pumped. As shown in FIG. 6 by way of example, the check housing may include four bores 290 each having a diameter of about 0.047 inches to provide a combined flow area of 0.007 in². The slightly larger cross-sectional area of the bores 290 compared to that of the tube 266 allows any excessive external ground water pressure to force the check ball 294 to seal off the nozzle 268 from ground water contamination. It is to be understood, however, that the number, pattern, and size of the bores 290 through the face 288 of the check housing 288 may be configured to assure adequate diffusion of the indicator reagent 271 into the surrounding soil at for example, a pressure which preferably is greater than about 100 psig.

Indicator reagent 271 may include compounds that form either colored or fluorescent complexes with the analyte (chemical or biological) to be analyzed. Examples of fluorescent indicator reagents 271 that are specific for the nucleic acids contained in microbiological organisms. Specific examples of such fluorescent indicators, or nucleic acid stains, include the cell-permeant SYTO® indicator reagents for labeling DNA and RNA in living cells including mammalian cells, fungi and bacteria. Other examples of florescent indicator reagents include cell-impermeant SYTOX® Green nucleic acid stains that penetrate cells with compromised plasma membranes. SYTO® indicator reagents and SYTOX® Green nucleic acid stains are available from Molecular Probes, Inc. of Eugene, Oregon. Fluorescent indicators that may be used to detect the presence of nucleic acids include, by way of example, hexidium iodide (a lipophilic phenthridiium dye) and hydroxystilbamidine.

It is also possible to use a fluorescent dye to enhance detection of NAPL contaminants in subsurface environments. Examples include the aminonapthalenesulfonates that are weakly fluorescent in water but exhibit strong fluorescence in non-polar solvents. Several long-chain dialkycarbocyanines can also be used to render non-aqueous phase compounds fluorescent. There is also a class of fluorescent indicator dyes called solvatochromic dyes that change their fluorescent emission signature when they are dissolved in different solvents. Nile Red is an example of a solvatochromic dye (in TCE Nile Red fluoresces at approximately 560 nm, in an ethanol-water mixture Nile Red fluoresces at approximately 640 nm). In addition to fluorescent indicator reagents, there is also a family of "indicator reagents"based on the formation of colored coordination compounds. These compounds form "colored" rather than fluorescent complexes with a suitable analyte of interest. Ethylenediaminetetraacetic acid (EDTA) is an example of an indicator reagent that forms colored complexes with metals such as copper. Nitrilotriacetic acid (NTA) is an example of an indicator reagent that forms colored complexes with metals such as nickel and copper. An example of colormetric indicator dye for detection of TCE is tri-iodide. (Dilute aqueous solutions of tri-iodide are pale yellow in color. When an aqueous solution of tri-iodide is added to a soil sample that contains immiscible globules of TCE, the iodine portion of the tri-iodide anion dissolves into the TCE causing the globules to become purplish red in color.)

There are several variations on how the images can be collected for this detection method. The most basic method implements light source 204 as a broad band visible light source for illuminating the soil in contact with optically transparent window 224 on the imaging system 240. Visible light generally is considered to be characterized as having a wavelength in the range of about 400–700 nanometers. The soil then is imaged through a lens system 232 to imaging system 240 which is located within tube 248. Alternatively, if a fluorescent indicator dye is used, light source 204 may implemented as either an ultra-violet (UV) or visible light source for exciting the fluorescent dye. Ultraviolet light has a wavelength of about 400 nanometers or less. The resulting fluorescence emissions can be detected by imaging system 240. Optical filter 236 may be used to select a spectral band of interest from the emissions. This would be particularly useful when used in conjunction with a colormetric indicator dye that renders the NAPL phase a specific color or when using a fluorescent indicator dye that emits at a specific spectral band.

Because the NAPLs are by definition immiscible in water they tend to form globules when they are present in soil that is saturated with water. These globules can often be identified in the video images by simple visual inspection due to their unique spherical or nearly spherical shape. Another distinguishing characteristic that can be used to identify these globules is their fluid motion that can be visually observed in the video images as the probe is pushed into the ground. As an alternative to visual inspection, it is also possible to use automated image processing techniques such as segmentation and object identification to automatically identify these objects in the images.

In order to account for the possible variations in the amount of indicator reagent which may be dispensed into the surrounding soil structure, a chemical tracer 273 which is nonreactive with the analyte can be added to the indicator reagent and stored in reservoir 274 (FIG. 3). Thus, both an indicator reagent 271 and chemical tracer 273 may be dispensed from pump system 264 of FIG. 1. The nonreactive chemical tracer 273 is preferably spectroscopically distinguishable from the indicator reagent and analyte (species of interest) and is used to normalize the optical response due to differences in the concentration of indicator reagent 271 present in the soil. Such normalization may be determined from the ratio of the intensities of the spectral responses of the complex (the chemical product of the analyte and indicator reagent) and the chemical tracer 273. Examples of tracer chemicals are rhodamine 6G and quinine sulfate.

The inventive method does not require removal of the sample from the subsurface soil environment. Therefore, the behavior of contaminants can be observed under ambient conditions (e.g., pressure, temperature, etc.) with only minimal disruption from insertion of the probe system 200. Another advantage of this method is that because data is collected nearly continuously, small-scale spatial variability in the distribution of the contaminant can be easily delineated. In contrast, traditional analysis methods that rely on collection of discrete samples may often miss zones of contamination because of inadequate sampling. Also, the images may also provide information on the lithology in which the contamitnant resides. This information may be used to define lithogolical units that may serve as transport paths or, conversely, barriers to migration of the contamination. Although the invention has been described with reference to specific embodiments, numerous variations and modifications of the invention may become readily apparent to those skilled in the art in light of the above teachings. For example, the inventive method may employ chemical indicator reagents that produce either a decrease or increase in an optical signal for an analyte of interest. Examples of alternative indicators include: (1) reagents that produce chemiluminescent signals without external optical stimulation; and (2) reagents that quench the specific fluorescence of the analyte of interest. Furthermore, the light source and/or pump system, including the reservoir may be mounted within the probe, or externally with respect to the probe. Further, the reagent could be pumped from the surface to outlet ports on the probe, or be contained in a reservoir mounted within the probe itself. Additionally, the pump system may be used to dispense one or more indicator reagents in combination or serially, as well as one or more tracer compounds. While the invention has been described for purposes of illustration with reference to subsurface terrestial environments, the scope of the invention includes subsurface aqueous environments. Therefore, it is to be understood that the invention may be practiced other than as specifically described.

We claim:

1. A method for detecting materials in a subsurface soil environment, comprising the steps of:
    penetrating said subsurface soil environment with a tube having a conically shaped tip;
    injecting a non-fluorescent reagent from said tube into said subsurface soil environment so that said reagent and a non-fluorescent chemical constituent of interest directly contacted with said reagent chemically interact, thereby forming a fluorescent product;
    producing a fluorescent optical response signal when said fluorescent product is illuminated with optical energy directed from said tube; and
    imaging said fluorescent optical response signal.

2. The method of claim 1 wherein said reagent is selected from the group that includes aminonapthalensulfonates, dialkycarbocyanines, solvatochromic dyes, and nucleic acid stains.

3. The method of claim 1 wherein said optical energy includes visible light.

4. The method of claim 1 wherein said optical energy includes ultraviolet light.

5. The method of claim 1 further including the steps of: injecting a chemical tracer into said subsurface soil environment that is spectroscopically distinguishable from said reagent and said chemical constituent of interest; and normalizing said fluorescent optical response signal.

6. A method for detecting materials in a subsurface soil environment, comprising the steps of:
   penetrating said subsurface soil environment with a tube having a conically shaped tip;
   injecting a non-fluorescent reagent from said tube into said subsurface soil environment so that said reagent and a non-fluorescent, non-aqueous phase liquid of interest directly contacted with said reagent chemically interact, thereby forming a fluorescent product;
   producing a fluorescent optical response signal when said fluorescent product is illuminated with optical energy directed from said tube; and
   imaging said fluorescent optical response signal.

7. The method of claim 6 wherein said reagent is selected from the group that includes aminonapthalensulfonates, dialkycarbocyanines, and solvatochromic dyes.

8. The method of claimed 6 wherein said optical energy includes visible light.

9. The method of claim 6 wherein said optical energy includes ultraviolet light.

10. The method of claim 6 further including the steps of: injecting a chemical tracer into said subsurface soil environment that is spectroscopically distinguishable from said reagent and said non-aqueous phase liquid of interest; and normalizing said fluorescent optical response signal.

11. A method for detecting materials in a subsurface soil environment, comprising the steps of:
    penetrating said subsurface soil environment with a tube having a conically shaped tip;
    injecting a non-fluorescent reagent from said tube into said subsurface soil environment so that said reagent and a non-fluorescent microbiological organism of interest directly contacted with said reagent chemically interact, thereby forming a fluorescent product;
    producing a fluorescent optical response signal when said fluorescent product is illuminated with optical energy directed from said tube; and
    imaging said fluorescent optical response signal.

* * * * *